(12) United States Patent
Ohga et al.

(10) Patent No.: US 8,231,843 B2
(45) Date of Patent: Jul. 31, 2012

(54) AUTOMATIC ANALYZER

(75) Inventors: Hiroshi Ohga, Hitachiohmiya (JP); Masato Ishizawa, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/180,084

(22) Filed: Jul. 11, 2011

(65) Prior Publication Data

US 2011/0267198 A1    Nov. 3, 2011

Related U.S. Application Data

(63) Continuation of application No. 12/200,427, filed on Aug. 28, 2008, now abandoned.

(30) Foreign Application Priority Data

Aug. 31, 2007  (JP) .................................. 2007-224993

(51) Int. Cl.
*B01L 3/00*    (2006.01)

(52) U.S. Cl. .......... 422/501; 422/50; 422/500; 422/502; 73/863; 73/864.11

(58) Field of Classification Search .......... 422/500–502, 422/50; 73/864.11, 863
See application file for complete search history.

(56) References Cited

U.S. PATENT DOCUMENTS 5,723,795 A * 3/1998 Merriam ......................... 73/863

FOREIGN PATENT DOCUMENTS

| EP | 1 669 762 A1 | 6/2006 |
|----|----|----|
| JP | 10-227799 | 8/1998 |
| JP | 2003-254982 | 9/2003 |
| JP | 2005-017144 | 1/2005 |

\* cited by examiner

*Primary Examiner* — Jyoti Nagpaul

(74) *Attorney, Agent, or Firm* — Mattingly & Malur, PC

(57) ABSTRACT

Pressure fluctuations are sampled at fixed time intervals and subjected to arithmetic processing, using as a trigger the event (or a sign temporally close to that event) of the reverse motor rotation for the backlash correction, thereby discriminating normal suction from suction of sample liquid with undesirable air bubbles.

5 Claims, 3 Drawing Sheets

AUTOMATIC ANALYZER

INCORPORATED BY REFERENCE

This application is a continuation of U.S. patent application Ser. No. 12/200,427, filed Aug. 28, 2008 which claims priority to Japanese Patent Application No. 2007-224993, filed Aug. 31, 2007, which is incorporated herewith by reference in its entirety.

BACKGROUND OF THE INVENTION

1. Field of the Invention

The present invention relates to an automatic analyzer which performs qualitative and quantitative analysis of biogenic substances such as blood, urine, etc. More particularly, the present invention relates to an automatic analyzer having a pipetting device including a nozzle for suctioning and discharging a sample, a syringe, a pipe, and a pressure sensor for monitoring the pressure in the pipe.

2. Description of the Related Art

Automatic analyzers in general pipette a sample such as blood, urine, cerebrospinal fluid, etc. from a test tube or a certain vessel for that purpose to a reaction vessel, mix the sample with a reagent to cause a reaction between the sample and reagent, and measure components contained in the sample by use of measurement means such as a photometer.

During sample pipetting, the nozzle of the pipetting device is inserted into the sample in the test tube or dedicated vessel, and the syringe is driven to pipette a particular amount of the sample, which amount is predetermined and stored in a calculation unit on a measurement-item-by-item basis.

Pipetting devices of recent automatic analyzers commonly detect the liquid surface of a sample by capacitance variation, stops the lowering operation of the nozzle immediately after it is inserted into the liquid surface, and sucks the sample. Since a biological sample having viscosity is commonly used as a sample, handling or storing it in the wrong way may cause air bubbles on its liquid surface. These air bubbles may cause incorrect detection of the liquid surface.

In this case, air may be sucked together with the sample, and an expected amount of the sample may not be sucked.

If the sample is measured while the expected amount of the sample cannot be sucked because of incorrect detection of the liquid surface, correct measurement results may not be obtained. As means for avoiding this, a technique disclosed in patent literature, JP-A-10-227799, provides two pressure sensors at different positions (one in the vicinity of the nozzle and the other in the vicinity of a pump) to detect sucked air based on the difference in pressure fluctuation between the two positions.

SUMMARY OF THE INVENTION

With the technique described in the patent literature, providing two pressure sensors at different positions increases the manufacture costs and the size of the pipetting device. Also, for pressure measurement, the technique uses an averaged, large time constant in order to eliminate noise. If the amount of sample liquid to be pipetted is several tens of microliters, which is the pipetting amount of the automatic analyzer according to the present invention, pressure fluctuation cannot be correctly detected.

An object of the present invention is thus to provide an automatic analyzer which includes means for correctly detecting whether or not air is sucked even when a minute amount (several microliters) of sample liquid is to be pipetted.

In order to attain the above-mentioned object, the present invention is configured as follows.

An automatic analyzer for pipetting a sample liquid into a reaction vessel to analyze the sample liquid, the analyzer comprising:
  a pipetting device having
    a nozzle for suctioning a sample liquid,
    a syringe and a driving source thereof for generating pressure to suction the sample liquid into the nozzle and discharge the sample liquid from the nozzle, and
    a pipe for connecting the nozzle and the syringe; and
  pressure measurement means for measuring the pressure inside the pipe;
  wherein the automatic analyzer includes:
  storage means for storing a pressure fluctuation for each amount of sample liquid suctioned;
  calculation means for performing a comparing process or an arithmetic process to the pressure fluctuations stored in the storage means; and
  detection means for detecting whether or not an air bubble is present inside the pipe by using the calculation means for comparing a pressure fluctuation detected by the pressure measurement means during a predetermined period of time with a stored pressure fluctuation stored in the stored means, the detection mean using as a trigger for the detection a syringe operation during the normal suctioning operation of the nozzle to compare the pressure fluctuation detected by the pressure measurement means with the stored pressure fluctuation in the storage means.

Further, the automatic analyzer detects the suction of air bubbles by observing the amplitude (height and width) of pressure fluctuation at the time of sudden reverse rotation of a motor (driving source), which reverse rotation is performed to correct a suction error caused by the jolting motion of a gear of a syringe drive unit during sample suction operation.

The present invention makes it possible to detect a minute amount of air bubbles during suction operation, inform an operator of whether or not an air bubble is present inside the pipe, and improve the reliability of results of measurement performed with a minute amount of sample liquid.

DETAILED DESCRIPTION OF THE PREFERRED EMBODIMENTS

Figure 1:
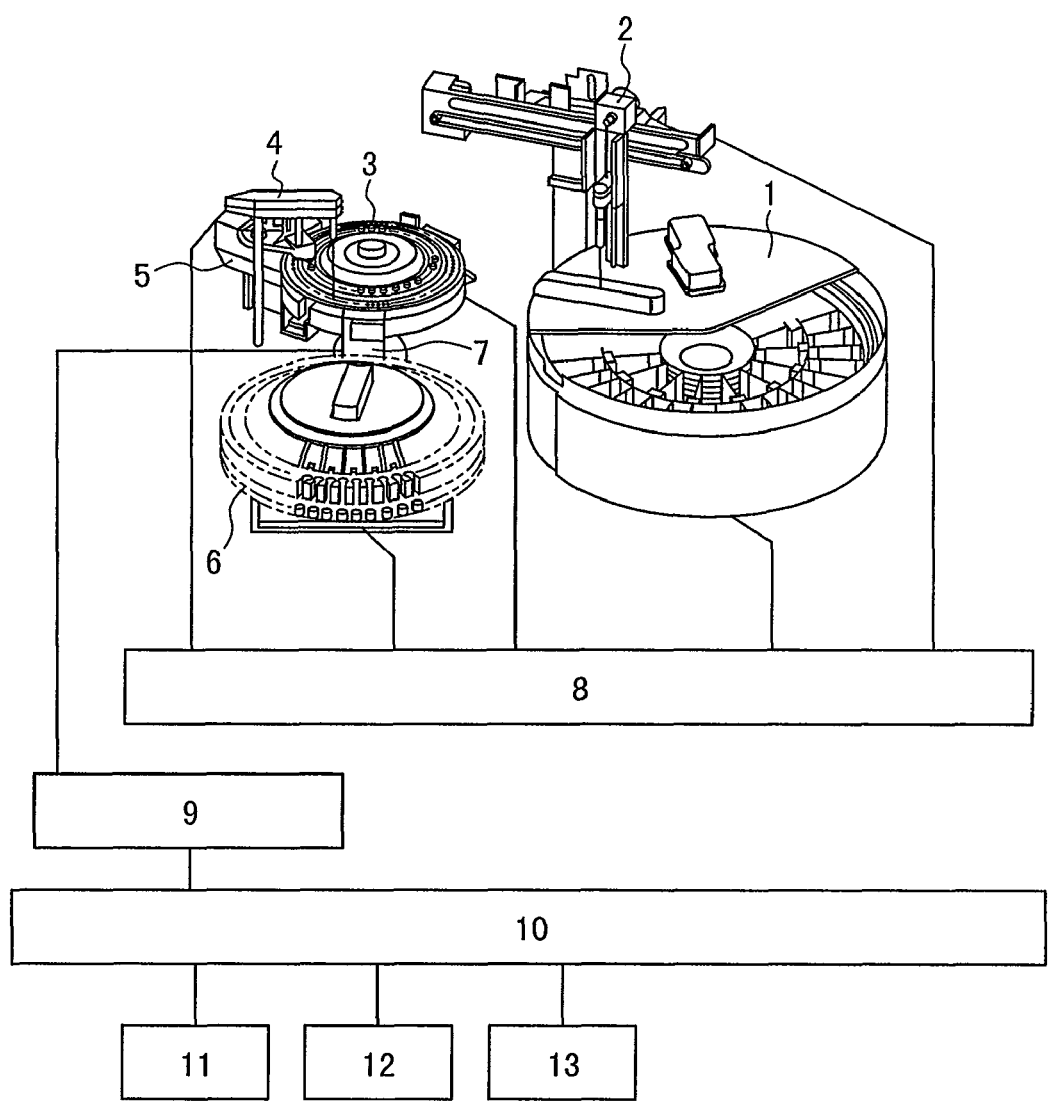
FIG. 1 is a schematic diagram of an automatic multi-purpose analyzer.

FIG. 1 is a schematic diagram of an automatic analyzer which incorporates a pipetting device according to an embodiment of the present invention.

The automatic analyzer shown in FIG. 1 is composed mainly of a reagent disk 1, a reagent pipetting mechanism 2, a reaction disk 3, a sample pipetting mechanism 4, a photometer 5, a sample disk 6, an ultrasonic mixing unit 7, a mechanism drive unit 8, an ultrasonic wave generator drive unit 9, a control unit 10, a storage device 11, an input unit 12, and a display unit 13.

The reagent disk 1 circumferentially installs therein vessels each containing a reagent to be mixed with a sample for reaction and circumferentially moves to an intended position by means of the control unit 10 and the mechanism drive unit 8. The reagent pipetting mechanism 2 pipettes a reagent from a reagent vessel installed on the reagent disk 1 and discharges it into the reaction disk 3. The reagent pipetting mechanism 2 is composed of a nozzle for suctioning a reagent, a motor or the like for horizontally moving the nozzle, and another motor or the like for vertically moving the nozzle. The sample disk 6 installs thereon samples each contained in a vessel such as a test tube, circumferentially rotates, and is circumferentially moved by the control unit 10 and the mechanism drive unit 8. The sample pipetting mechanism 4 pipettes a sample and discharges that sample into the reaction disk 3. The reaction disk 3 is circumferentially rotated to a predetermined position by a motor driven by the mechanism drive unit 8 and the control unit 10. The ultrasonic mixing unit 7 mixes the sample and reagent. The photometer 5 measures components of the sample. The storage device 11 stores information necessary for drive system control and information necessary for analysis and exchanges information with a computer (not shown). The input unit 12 is used by an operator to input parameters or the like and typically represented by an input device such as a keyboard. The display unit 13 displays various screens such as analysis items, analysis results, and the like.

Figure 2:
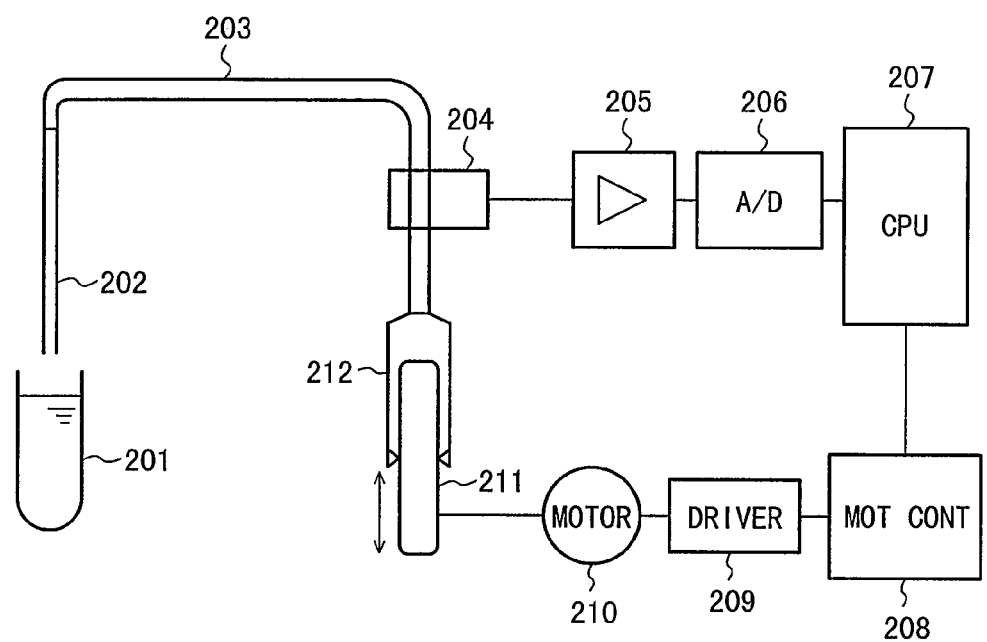
FIG. 2 is a block diagram of a pressure detection system.

An embodiment of the present invention will be described below with reference to FIG. 2.

Reference numeral 201 denotes a test tube which contains a sample. The pipetting device according to this embodiment is composed mainly of a nozzle 202, a pipe 203, a pressure sensor 204, an amplifier 205, an analog-to-digital converter 206, a CPU 207, a motor controller 208, a motor driver 209, a motor 210, a plunger 211, and a syringe 212. The motor 210 moves the plunger 211 up and down, controlled by the motor controller 208 and the motor driver 209 based on a command from the CPU 207. The up-and-down motion of the plunger 211 causes the nozzle 202 to suction the sample in the test tube 201. The pressure sensor 204 converts a pressure fluctuation inside the pipe 203 to an analog signal, which is amplified by the amplifier 205. The amplified analog signal is input to the analog-to-digital converter 206, where it is converted into a digital signal. The digital signal is then subjected to storage and arithmetic processing at the CPU 207.

A concrete method for detecting sucked air upon suction of a sample will be explained below with reference to FIG. 3.

Figure 3:
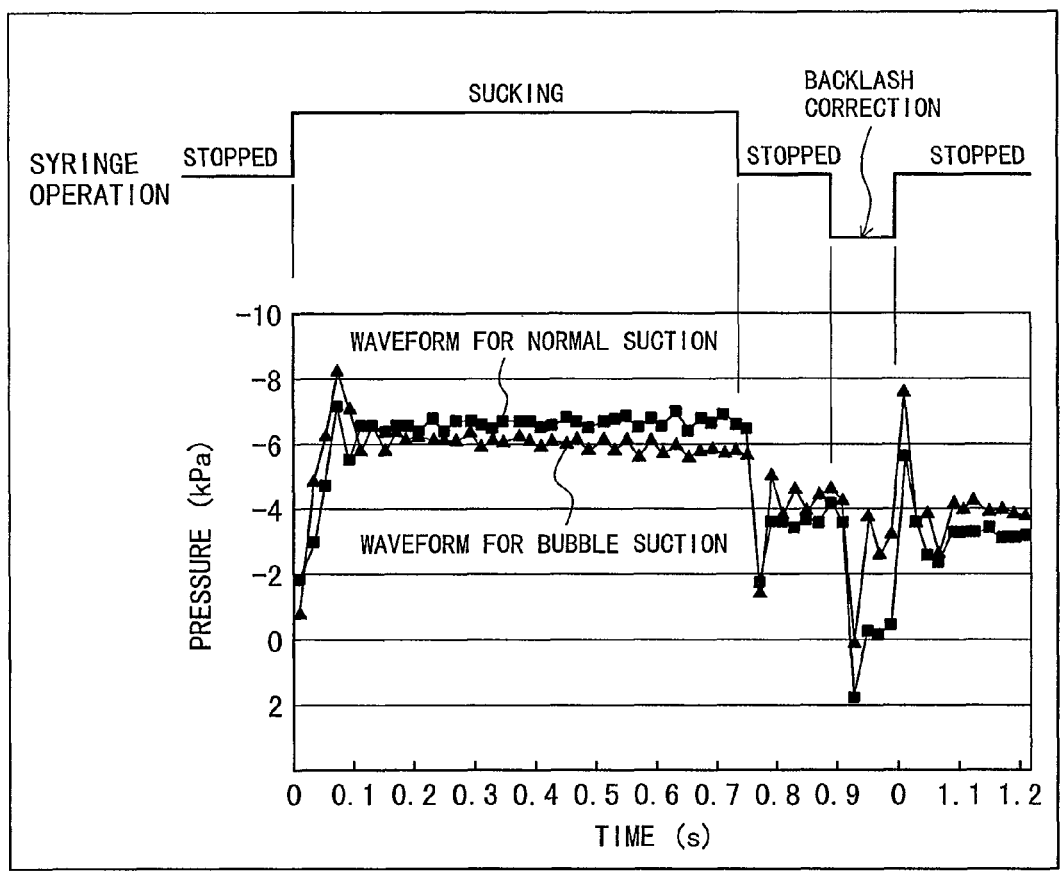
FIG. 3 shows a pressure fluctuation waveform upon normal suction and a pressure fluctuation waveform upon suction of air bubbles.

FIG. 3 is a graph showing pressure fluctuation when the sample is suctioned.

The operation of the syringe and pressure fluctuation will be now explained. During suction operation, the pressure inside the pipe becomes negative. After the syringe stops to operate, the pressure will then return to zero. At this time, however, the motor driving the syringe reversely rotates for backlash correction and then stops. Although this operation lasts for about 100 milliseconds, the movement of the sample cannot respond to the sudden operation of the syringe during the backlash correction because of the viscosity of the sample inside the pipe, thus showing large overshoot and undershoot of the pressure value. When air bubbles are present inside the pipe, the pressure inside the pipe during the backlash fluctuates differently from that during normal suction because of the cushioning effects of the air bubbles. In the present invention, pressure fluctuations are sampled at fixed time intervals and subjected to arithmetic processing, using as a trigger the event (or a sign temporally close to that event) of the reverse motor rotation for the backlash correction, thereby discriminating normal suction from suction of air bubbles.

Specifically, the sampling period is 10 to 40 milliseconds, and in the arithmetic processing, a threshold value having a fixed margin is determined with reference to an integration value for normal suction in order to detect suction of air bubbles.

When the suction of air bubbles is detected, the operator can be notified of the detection with an alarm or by adding a comment or symbol to the measurement result.

What is claimed is:

1. A method of detecting the presence of an air bubble in a pipe used in an automatic analyzer including a nozzle for sucking or discharging a sample, a syringe having a plunger for generating pressure to suck the sample into the nozzle and discharge the sample from the nozzle, a pipe for connecting the nozzle and the syringe, pressure measurement means for measuring the pressure inside the pipe, storage means for storing a pressure fluctuation measured inside the pipe, and a motor for moving the plunger of said syringe, said method comprising the steps of:

measuring a pressure fluctuation within a predetermined period of time during operation of a sample suctioning into the nozzle or a sample discharging from said nozzle, said pressure fluctuation being measured by said pressure measuring means;

storing said pressure fluctuation into said storage means, and;

detecting whether or not an air bubble is present inside the pipe on the basis of a pressure fluctuation at a reverse rotation of said motor for compensating a backlash of said syringe, where said pressure fluctuation at said reverse rotation is stored in said storage means.

2. The method according to claim 1, wherein said predetermined period of time is 10 to 40 milliseconds for sampling said pressure fluctuation measured by said pressure measurement means.

3. The method according to claim 1, wherein pressure fluctuations measured by said pressure measurement means are integrated during said reverse rotation of said motor to obtain an integrated pressure fluctuation, and said detection means compares a threshold value with said integrated pressure fluctuation to determine whether or not an air bubble is present inside the pipe.

4. The method according to claim 3, wherein said threshold value is determined on the basis of an integration value of pressure fluctuations measured by said pressure measurement means during said reverse rotation of said motor at a normal suction operation where no air bubble is mixed into the pipe.

5. The method according to claim 1, further comprising the step of notifying the detection of the suction of air bubbles by said detection means to an operator by using an alarm.

* * * * *